United States Patent [19]
Stöckemann et al.

[11] Patent Number: 6,043,234
[45] Date of Patent: *Mar. 28, 2000

[54] METHOD FOR TREATING ENDOMETRIOSIS OR LEIOMYOMATA UTERI WITH A COMPETITIVE PROGESTERONE ANTAGONIST AND A GESTAGEN

[75] Inventors: Klaus Stöckemann; Kristof Chwalisz, both of Berlin, Germany

[73] Assignee: Schering Aktiengesellschaft, Berlin, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,152

[22] PCT Filed: Jul. 27, 1995

[86] PCT No.: PCT/EP95/02998

§ 371 Date: Jun. 10, 1997

§ 102(e) Date: Jun. 10, 1997

[87] PCT Pub. No.: WO96/03130

PCT Pub. Date: Feb. 8, 1996

[30] Foreign Application Priority Data

Jul. 27, 1994 [DE] Germany .............................. 44 26 601

[51] Int. Cl.[7] ...................................... A61K 31/56
[52] U.S. Cl. .............................................. 514/170
[58] Field of Search ............................... 514/170

[56] References Cited

PUBLICATIONS

CA 102:40106, Azadian–Boulanger et al. 1984.

CA 120:253388, Lipp et al. Mar. 1994.

*Primary Examiner*—Kimberly Jordan
*Attorney, Agent, or Firm*—Millen, White, Zelano, & Branigan, P.C.

[57] ABSTRACT

This invention relates to the use of a product that contains in combination individual dosage units of a competitive progesterone antagonist and individual dosage units of a gestagen for its sequential, oral administration, in which each individual dosage unit that contains the competitive progesterone antagonist contains the latter in a non-abortion-inducing amount for the production of a pharmaceutical agent for treating endometriosis or leiomyomata uteri.

13 Claims, No Drawings

METHOD FOR TREATING ENDOMETRIOSIS OR LEIOMYOMATA UTERI WITH A COMPETITIVE PROGESTERONE ANTAGONIST AND A GESTAGEN

This application is a 371 of PCT/EP95/02998, filed Jul. 27, 1995.

This invention relates to the use of a combination product that consists of individual dosage units of a competitive progesterone antagonist and individual dosage units of a compound that are provided sequentially in it, having a gestagenic action for the production of a pharmaceutical agent for treating endometriosis or leiomyomata uteri.

It is known that competitive progesterone antagonists (antigestagens=AG's) such as, e.g., RU486 (mifepristones; 11β-[(4-N,N-dimethylamino)-phenyl]-17β-hydroxy-17α-propinyl-4,9(10)-estradien-3-one) are able to inhibit ovulation in various animal species and in women [1) Uilenbroek, J. TH. J.(1991); Hormone Concentrations and Ovulatory Response in Rats Treated with Antiprogestagens. Journal of Endocrinology, 129, 423–429; 2) Danforth, R. et al (1989): Contraceptive Potential of RU486 by Ovulation Inhibition: III. Preliminary Observations on Once Weekly Administration, Contraception, 40/2, 195–200; 3) Kekkonen, R. et al. (1990): Interference with Ovulation by Sequential Treatment with the Antiprogestin RU486 and Synthetic Progestin. Fertility and Sterility, 53/4, 747–750; 4) Ledger, W. L. et al. (1992): Inhibition of Ovulation by Low Dose Mifepristone (RU486). Human Reproduction, 7/7, 945–950; 5) Nieman, L. K. et al. (1987): The Progesterone Antagonist RU486: A New Potential New Contraceptive Agent. The New England Journal of Medicine, 316/4, 187–1991].

The implantation of a fertilized egg can also be prevented by AG's (implantation inhibition); [6) Glassier A. et al. (1992): Mifepristone (RU 486) Compared with High Dose Estrogen and Progesterone for Emergency Postcoital Contraception: New England Journal of Medicine, 8/15; 1041; 7) Puri, C. P. et al. (1990); Effects of a Progesterone Antagonist, Ilopristone, On Induction of Menstruation, Inhibition of Nidation, and Termination of Pregnancy in Bonnet Monkeys. Biology of Reproduction, 43, 437–443; 8) Ishwad, P. C. et al. (1993): Treatment with a Progesterone Antagonist ZK 98 299 Delays Endometrial Development without Blocking Ovulation in Bonnet Monkeys. Contraception, 48, 57–70; 9) Batista, M. C. et al. (1992): Delayed Endometrial Maturation Induced by Daily Administration of the Antiprogestin RU 486: A Potential New Contraceptive Strategy. AM. J. Obstet. Gynecol. 167/1, 60–65].

It should be possible to use AG's as contraceptive agents because of their ovulation-inhibiting [3), 4), 5)] or implantation-inhibiting action [6), 7), 8), 9)]. The use of competitive progesterone antagonists at a non-ovulation-inhibiting as well as a non-abortion-inducing dose for the production of oral contraceptive agents is described in International Patent Application WO-A 93/23020.

In addition, for gynecological applications, initial clinical studies have shown that AG's can be used for treating endometriosis and leiomyomata uteri (myoma) [10) Kettel, L. M. et al. (1991): Endocrine Responses to Long-Term Administration of the Antiprogesterone RU 486 in Patients with Pelvic Endometriosis. Fertility and Sterility, 56/3, 402–407; 11) Kettel, L. M. et al. (1993): Long-Term, Low-Dose RU486 in the Treatment of Endometriosis. Meeting of the Society of Gynecological Investigation 1993, Abstract p. 136; 12) Murphy, A. A. et al. (1993): Regression of Uterine Leiomyomata in Response to the Antiprogestin RU486, J. Clin. Endocrinol. Metab., 76/2, 513–517].

The findings from these studies also indicate, however, that in the case of chronic treatment with AG's over the entire menstrual cycle, but also in the case of treatment during certain cycle phases with AG's, alteration or lengthening of the cycle with cessation of monthly bleeding (amenorrhea) or reduced menstruation can occur because of the elimination of progesterone action during the luteal phase of the cycle [8), 9), 10)].

Monthly bleeding means, however, natural protection for the endometrium. In the normal menstrual cycle, proliferation of the endometrium results in the follicle phase (proliferation phase) under the action of estrogens. Subsequently, growth endometrium inhibition that is caused by progesterone takes place in the luteal phase (secretion phase), with conversion into a secretorily active endometrium. At the end of this phase, monthly bleeding of the endometrium occurs, during which portions of this tissue are shed.

If, however, during treatment with a competitive progesterone antagonist the action of progesterone on the endometrium is completely blocked in the luteal phase, the proliferative influence of the estrogens on the endometrium predominates. In addition to the cessation of conversion into a secretory endometrium and the thus deficient [10)] subsequent bleeding (induction of an amenorrhea) or reduced bleeding [8)], continuous stimulation of the endometrium can then occur owing to the so-called "unopposed estrogen effect" [13a) Murphy, A. A. et al. (1993): Endometrial Effect of a Long-Term, Low-Dose Administration of RU 486 in Cycling Women. Meeting of the Society of Gynecological Investigation 1993, Abstract p. 138; 13b) Murphy, A. A.; Kettel, L. M.; Morales, A. J.; Roberts, V.; Parmely, T.; Yen, S. S. C. (1995) Endometrial Effects of Long-Term Low-Dose Administration of RU 486. Fertility Sterility. 63: 761–766].

This can increase the risk of endometrial hyperplasia or the development of an endometrial carcinoma [14) Galle, P. C. and McRae, M. A. (1992): Amenorrhea and Chronic Anovulation. Finding and Addressing the Underlying Cause. Postrad. Med., 92/2, 255–260; 15) Johansson, E. D. et al. (1981): Unopposed Endogenous Estrogens and the Incidence of Cancer in Female Reproductive Organs. Acta. Obstet. Gynecol. Scand. Suppl., 101, 17–20].

Despite the growth-inhibiting action of the progesterone antagonist on myoma [12)] and endometriosis [11)], an undesirable stimulation of the epithelium in the endometrium can occur [13)], possibly caused by the so-called "unopposed estrogen effect." Under certain circumstances this could pose a risk (chronic stimulation→risk or development of endometrial carcinoma) for long-term treatment with progesterone antagonists alone or prevent development of preparations.

The object of the invention is to provide a pharmaceutical agent for the above-indicated indications which has none or very few of the undesirable side-effects that occur when these diseases are continuously treated with competitive progesterone antagonists, such as, e.g., persistent amenorrhea, endometrial hyperplasia, etc., so that a more efficient and reliable treatment, as well as better cycle control are ensured and, in the case of long-term treatment, a protective function is exerted on the endometrium.

This object is achieved by the use, according to the invention, of a product that contains in combination in a packaging unit individual dosage units of a competitive progesterone antagonist and individual dosage units of a gestagen for its sequential, oral administration, in which case each individual dosage unit that contains the competitive progesterone antagonist contains the latter in a non-abortion-inducing amount, dissolved, for the production of a pharmaceutical agent for treating endometriosis or leiomyomata uteri.

The dosage of the competitive progesterone antagonist can be in both the ovulation-inhibiting and the non-ovulation-inhibiting range of this antagonist.

The sequential administration of a gestagen during the break in treatment with the competitive progesterone antagonist ensures that the endometrium is transformed and converted into a secretorily active endometrium.

If the competitive progesterone antagonist in the combination product is present at a non-ovulation-inhibiting dose, the latter does not interfere with ovulation. When a non-ovulation-inhibiting dosage is used, impairment of the ovarian cycle is therefore avoided. Subsequent to an AG administration, the endometrium is prepared by the gestagen—corresponding to the normal cycle in the luteal phase—for bleeding induced by the progesterone antagonists that are administered after the administration of gestagen (see Diagram 1).

The progesterone antagonist acts.in a growth-inhibiting manner according to this invention either based on the ovulation inhibition or—when a non-ovulation-inhibiting dosage is used—by acting directly on the target tissue (endometriosis focus/myoma). Since complete suppression of the estrogens does not occur with treatment with a competitive progesterone antagonist [the levels are comparable to those in the middle follicle phase (10)], subsequent to the AG treatment the endometrium is converted by a gestagen (corresponding to the normal cycle) and is prepared for bleeding that corresponds to the natural period, which is induced by the continued AG treatment.

The fact that bleeding can be induced by competitive progesterone antagonists has been described [5]. This is also possible in the presence of progesterone [16] Croxatto H. B.; Spitz, I. M.; Salvatierra, A. M. and Bardin, C. W. (1985). The Demonstration of the Antiprogestin Effects of RU 486 When Administered to the Human During hCG-induced Pseudopregnancy. In Baulieu E. E. and Segal, S. J. (eds.). The Antiprogestin Steroid RU486 and Human Fertility Control. Plenum Press, New York, pp. 263–269). Suitable cycle control is ensured by sequential treatment with gestagen.

With the proposed composition, the undesirable effects of possible monotherapy with a competitive progesterone antagonist (chronic amenorrhea and stimulation of the endometrium) can be prevented.

By providing a break in treatment with the competitive progesterone antagonist of 2 to 12, preferably 5–10 days, during which a gestagen is administered at an effective dose for 2 to 12, preferably 5 to 10 days, the endometrium is prepared for bleeding (transformation into a secretory tissue). The subsequent continued treatment with a competitive progesterone antagonist simulates the natural drop in progesterone (progesterone blocking) and triggers menstruation, during which portions of the endometrium are shed. Owing to the regular daily administration of a gestagen over a specific period at an effective dose, e.g., every 28 days (length of an untreated cycle), or, e.g., at intervals that correspond to 3 or up to 6 normal untreated cycles, the endometrium is prepared for bleeding induction by a competitive progesterone antagonist. Thus, the manifestation of lasting amenorrhea or endometrial hyperplasia caused by the deficient conversion of the endometrium in the luteal phase, which can occur with chronic treatment with AG alone, is prevented and better cycle control is thus ensured. The endometrium is protected against the above-described effects by regular induction of bleeding (simulation of a natural bleeding).

Typical different embodiment possibilities of the composition are depicted in Diagrams 1, 2, and 3. The gestagen that is administered sequentially to the competitive progesterone antagonist is provided in the product that is to be used according to the invention preferably at the earliest for administration starting from day 15 and especially starting from day 18 after the first administration of the competitive progesterone antagonist.

The number of dosage units of the competitive progesterone antagonist that are to be administered, as well as the number of the gestagen-containing dosage units that are subsequently to be administered daily, can be selected such that the menstrual bleeding that is triggered by the administration of gestagen corresponds in time to the menstrual bleeding in an untreated cycle (Diagram 1)).

The combination product that is to be used according to the invention can contain the dosage units of the gestagen that are to be administered sequentially to the competitive progesterone antagonist arranged in such a way that they are provided at the latest after 6×28-day (corresponds to the period of 6 normal, untreated cycles) administration of the progesterone antagonist (Diagram 3)).

Between these two limits (competitive progesterone antagonist with a period of 15 or 6 times 28 days), all conceivable cases are possible, thus, e.g., 2×28-day administration of the competitive progesterone antagonist, then gestagen administration. As competitive progesterone antagonists according to this invention, all compounds are suitable which themselves or whose metabolic products block the action of the progesterone at its receptor. As typical representatives, the following can be mentioned as examples:

11β-((4-N,N-Dimethylamino)-phenyl)-17β-hydroxy-17α-propinyl-4,9(10)-estradien-3-one (RU-38486), 11β-((4-N,N-dimethylamino)-phenyl)-17β-hydroxy-18-methyl-17α-propinyl-4,9(10)-estradien-3-one, 11β-((4-N,N-dimethylamino)-phenyl)-17αβ-hydroxy-17aα-propinyl-D-homo-4,9(10),16-estratien-3-one, 11β-p-methoxyphenyl-17β-hydroxy-17α-ethinyl-4,9(10)-estradien-3-one (Steroids 37 (1981), 361–382), 11β-(4-acetylphenyl)-17β-hydroxy-17α-(prop-1-inyl)-4,9(10)-estradien-3-one (EP-A 0 190 759), the 19,11β-bridged steroids from EP-A-0 283 428, the 10β-H steroids from EP-A-0 404 283, 11β-[(4-dimethylamino)phenyl]-17α-hydroxy-17β-(3-hydroxypropyl)-13α-methyl-4,9(10)-gonadien-3-one (onapristone; EP-A-0 129 499);

11β-19-(4-acetylphenyl)-17β-hydroxy-17α-(3-hydroxyprop-1(Z)-enyl)-4,9(10)-estradien-3-one (EP-A-0 190 759);

11β,19-(4-(cyanophenyl)-17β-hydroxy-17α-(3-hydroxyprop-1(Z)-enyl)-4-androsten-3-one, 11β,19-(4-(3-pyridinyl)-o-phenylene)-17β-hydroxy-17α-(3-hydroxyprop-1(Z)-enyl)-4-androsten-3-one (both WO-A 93/23020);

6α,11β,17β)-11(4-dimethylaminophenyl)-6-methyl-4',5'-dihydrospiro[estra-4,9-diene-17,2'(3'H)-furan]-3-one;

(11β,17α),-11-(4-acetylphenyl)-17,23-epoxy-19,24-dinorchola-4,9,20-trien-3-one;

7β,11β,17β)-11(4-dimethylaminophenyl)-7-methyl-4',5'-dihydrospiro[estra-4,9-diene-17,2'(3'H)-furan]-3-one (all U.S. Pat. No. 4,386,085).

This list is not exhaustive; other competitive progesterone antagonists that are described in the above-mentioned publications, as well as those from publications that are not mentioned here, are also suitable.

For the purposes of this invention, the competitive progesterone antagonists can be administered locally, topically, enterally, transdermally, or parenterally.

For the preferred oral administration, especially tablets, coated tablets, capsules, pills, suspensions, or solutions are suitable, which can be produced in the usual way with the additives and vehicles that are commonly used in galenicals.

For local or topical use, for example, vaginal suppositories, vaginal gels, implants, vaginal rings, or transdermal systems, such as skin patches, are suitable.

One dosage unit contains about 0.01 to 100 mg of 11β-[(4-dimethylamino)phenyl]-17α-hydroxy- 17β-(3-hydroxypropyl)-13α-methyl-4,9(10)-gonadien-3-one (onapristone), 0.01–100 mg of 11β-((4-N,N-dimethylamino)-phenyl)-17β-hydroxy-17α-propinyl-4,9-(10)-estradien-3-one (RU 486), or a biologically equivalent amount of another competitive progesterone antagonist.

If the administration of the competitive progesterone antagonist that is to be used according to the invention is done by an implant, a vaginal ring, or a transdermal system, these administration systems must be designed so that the dose of the composition progesterone antagonist that is released by it daily lies in this range of 0.01 to 100 mg of 11β-[(4-dimethylamino)phenyl]-17α-hydroxy-17β-(3-hydroxypropyl)-13α-methyl-4,9(10)-gonadien-3-one or an equivalent-action dose of another progesterone antagonist. One-time administration is also to mean that when an administration system is used that releases the competitive progesterone antagonist continuously, 0.01–100 mg in each case is released per day.

The combination product that is to be used according to the invention for the production of a pharmaceutical agent for treating endometriosis or leiomyomata uteri preferably calls for the administration of the individual dosage units of the competitive progesterone antagonist daily, but only one administration every second or every third day may also be prescribed.

The combination product can also be structured so that the administration of the individual dosage units of the competitive progesterone antagonist is to be done every 4 to every 10 days.

In this case, the time intervals between the administrations of individual dosage units are preferably to be constant in each case.

In addition, the combination product may also call for administration of the respective dosage units of the competitive progesterone antagonist once per week, in each case on the same day of the week.

High intake reliability is ensured by administering it weekly on the same day in each case.

Equivalent-action dose amounts of various competitive progesterone antagonists are determined in the test for antigestagenic action on rabbits (elimination of the endometrium transformation).

As gestagens, all compounds according to this invention are suitable that are suitable for use in oral contraceptives owing to their gestagenic action. A list of such compounds is found in B. Runnebaum et al., "Female Contraception: Up-date and Trends," Springer-Verlag, Berlin, 1988, pages 64–90, 109–121, 122–128 and 129–140.

Preferred gestagens within the scope of this invention are gestodene, progesterone, levonorgestrel, cyproterone acetate, chlormadinone acetate, drospirenone (dihydrospirorenone), norethisterone, norethisterone acetate, norgestimate, desogestrel, or 3-ketodesogestrel.

The gestagen is present in the product according to this invention in a dosage form that is suitable for oral administration, namely as a tablet, coated tablet, capsule, or pill.

The formulation of the gestagen is done in this case in a way that is analogous to the preparation of gestagens for hormonal contraption using the adjuvants that are commonly used for this purpose.

A daily dosage unit of the gestagen contains the latter at a dose of 0.06–6.0 mg of levonorgestrel, 0.2–20 mg of cyproterone acetate, 0.03–3.0 mg of gestodene or 0.02–2.0 mg of desogestrel, or an amount of another gestagen that is equivalent in action to these dosages.

To determine equivalent-action dose amounts of various gestagens, known methods are used: further details are found in, for example, the two articles "Probleme der Dosisfindung: Sexualhormone [Problems of Dose-Finding: Sex Hormones]"; F. Neumann et al. in "Arzneimittelforschung [Pharmaceutical Agent Research]" 27, 2a, 296–318 (1977) as well as "Aktuelle Entwicklungen in der hormonalen Kontrazeption [Current Developments in Hormonal Contraception]"; H. Kuhl in "Gynäkologe [Gynecologist]" 25: 231–240 (1992).

EXAMPLES

```
Once per 28-day cycle of several days of gestagen:

1)
/----------1st cycle------/-----------2nd cycle-------/------3rd
cycle-------/etc.
Day:                         Day:                       Day:
1----AG----21/22----P---28/1----AG-----21/22---P---28/1----AG--21
/22---P---28
                                 ---> Bleeding         ---> Bleeding 2)
Day:                         Day:                       Day:
1----AG----23/24----P---28/1----AG----23/24---P---28/1----AG--23
/24---P---28
                                 ---> Bleeding         ---> Bleeding Once after three cycles (1 cycle = 28 days) of gestagen for
several days:
```

```
-continued
3)
/------1st cycle-----/------2nd cycle-----/------3rd cycle-----/
1--------AG--------28/1------AG--------28/1------AG----28/1---P--
10/11-----AG----28, etc.
                                                            ---->
Bleeding

0
```

AG stands for "competitive progesterone antagonist," and P stands for "gestagen"

We claim:

1. A method of treating endometriosis or leiomyomata uteri, comprising administering to a patient in need of such treatment a pharmaceutical agent comprising, in combination, individual dosage units of an effective amount of a competitive progesterone antagonist and individual dosage units of an effective amount of a gestagen, for sequential, oral administration, wherein the effective amount of each individual dosage unit of the competitive progesterone antagonist is a non-abortion-inducing amount.

2. A method of claim 1, wherein each individual dosage unit that contains the competitive progesterone antagonist is administered once daily to once weekly.

3. A method of claim 2, in which the dosage units of the competitive progesterone antagonist are administered once daily.

4. A method of claim 2, wherein the dosage units of the competitive progesterone antagonist are administered once weekly.

5. A method of claim 1, wherein the dosage units of the gestagen are administered daily on successive days.

6. A method of claim 5, wherein the pharmaceutical agent comprises 2 to 12 dosage units of gestagen.

7. A method of claim 6, wherein the dosage units of the gestagen are administered sequentially starting from day 15 or a later day after the first dosage unit of the competitive progesterone antagonist is administered.

8. A method of claim 6, wherein the dosage units of the gestagen are administered sequentially starting from day 18 or a later day after the first dosage unit of the competitive progesterone antagonist is administered.

9. A method of claim 6, wherein the dosage units of gestagen are administered starting from day 21 or 22.

10. A method of claim 1, wherein the dosage units that contain the competitive progesterone antagonist contain at least one compound selected from the group consisting of 11β-((4-N,N-Dimethylamino)-phenyl)-17β-hydroxy-17α-propinyl-4,9(10)-estradien-3-one (RU-38486), 11β-((4-N,N-dimethylamino)-phenyl)-17β-hydroxy-18-methyl-17α-propinyl-4,9(10)-estradien-3-one, 11β-((4-N,N-dimethylamino)-phenyl)-17αβ-hydroxy-17aα-propinyl-D-homo-4,9(10),16-estratien-3-one, 11β-p-methoxyphenyl-17β-hydroxy-17α-ethinyl-4,9(10)-estradien-3-one, 11β-(4-acetylphenyl)-17β-hydroxy-17α-(prop-1-inyl)-4,9(10)-estradien-3-one, 11β-[(4-dimethylamino)phenyl]-17α-hydroxy-17β-(3-hydroxypropyl)-13α-methyl-4,9(10)-gonadien-3-one (onapristone), 11β-19-(4-acetylphenyl)-17β-hydroxy-17α-(3-hydroxyprop-1(Z)-enyl)-4,9(10)-estradien-3-one, 11β,19-(4-(cyanophenyl)-17β-hydroxy-17α-(3-hydroxyprop-1(Z)-enyl)-4-androsten-3-one, 11β,19-(4-(3-pyridinyl)-o-phenylene)-17β-hydroxy-17α-(3-hydroxyprop-1(Z)-enyl)-4-androsten-3-one, 6α,11β,17β)-11(4-dimethylaminophenyl)-6-methyl-4',5'-dihydrospiro[estra-4,9-diene-17,2'(3'H)-furan]-3-one, (11β,17α)-11-(4-acetylphenyl)-17,23-epoxy-19,24-dinorchola-4,9,20-trien-3-one, 7β,11β,17β)-11(4-dimethylaminophenyl)-7-methyl-4',5'-dihydrospiro[estra-4,9-diene-17,2'(3'H)-furan]-3-one.

11. A method of claim 1, wherein each individual dosage unit that contains the competitive progesterone antagonist contains 0.01 to 100 mg of 11β-[(4-di-methylamino)phenyl]-17α-hydroxy-17β-(3-hydroxypropyl)-13α-methyl-4,9(10)-gonadien-3-one (onapristone), 0.01–100 mg of 11β-((4-N,N-dimethylamino)-phenyl)-17β-hydroxy-17α-propinyl-4,9(10)-estradien-3-one (RU 486) or a biologically equivalent amount of another competitive progesterone antagonist.

12. A method of claim 1, wherein the dosage units that contain the gestagen contain at least one compound selected from the group consisting of gestodene, progesterone, levonorgestrel, cyproterone acetate, chlormadinone acetate, drospirenone (dihydrospirorenone), norethisterone, norethisterone acetate, norgestimate, desogestrel, 3-ketodesogestrel or another artificial or natural gestagen.

13. A method of claim 1, wherein each individual dosage unit that contains the gestagen contains 0.06–6.0 mg of levonorgestrel, 0.2–20 mg of cyproterone acetate, 0.03–3.0 mg of gestodene, or 0.02–2.0 mg of desogestrel or a biologically equivalent amount of another gestagen.

* * * * *